United States Patent [19]

Glaeser et al.

[11] Patent Number: 4,801,727

[45] Date of Patent: Jan. 31, 1989

[54] METHOD FOR AMMOXIDATION OF PARAFFINS AND CATALYST SYSTEM THEREFOR

[75] Inventors: Linda C. Glaeser, Lyndhurst; James F. Brazdil, Jr., Mayfield Village; Mark A. Toft, Lakewood, all of Ohio

[73] Assignee: The Standard Oil Company, Cleveland, Ohio

[21] Appl. No.: 173,794

[22] Filed: Mar. 28, 1988

Related U.S. Application Data

[63] Continuation-in-part of Ser. No. 67,891, Apr. 20, 1987.

[51] Int. Cl.$^4$ .............................. C07C 120/14
[52] U.S. Cl. .................................... 558/319
[58] Field of Search ......................... 558/319

[56] References Cited

U.S. PATENT DOCUMENTS 3,833,638  9/1974  Knox et al. ............ 558/319

*Primary Examiner*—Joseph Paul Brust
*Attorney, Agent, or Firm*—C. S. Lynch; D. J. Untener; L. W. Evans

[57] ABSTRACT

Ammoxidation of $C_3$ to $C_5$ acyclic alkanes with $NH_3$ and $O_2$ using (1) a mole ratio of alkane:$NH_3$ in the range from 2 to 16 and a mole ratio of alkane:$O_2$ in the range 1 to 10 and (2) a mixture of particulate catalyst compositions, the first being especially effective to promote formation of an unsaturated nitrile and an olefin from the paraffin, and the second catalyst composition being especially effective to promote the conversion of the olefin to the unsaturated nitrile. Catalytic compositions useful in the process are disclosed.

18 Claims, No Drawings

METHOD FOR AMMOXIDATION OF PARAFFINS AND CATALYST SYSTEM THEREFOR

This is a continuation-in-part of Ser. No. 067,891, filed Apr. 20, 1987.

This invention relates to an improved process for the catalytic ammoxidation of paraffins containing from 3 to 5 carbon atoms to $\alpha,\beta$-unsaturated mononitriles, especially paraffins containing 3 to 4 carbon atoms. Most important is the ammoxidation of isobutane to methacrylonitrile and, especially, of propane to acrylonitrile.

Because of the price differential between propylene and propane an economic incentive exists for the development of a viable catalytic process for conversion of propane to acrylonitrile.

Earilier attempts in the prior art to develop an efficient process for the ammoxidation of propane to acrylonitrile produced either insufficient yields or processes that necessitated adding halogen promoters to the feed. The latter procedure would require not only reactors made of special corrosion resistant materials, but also the quantitative recovery of the promoter. The added costs thus eliminated the advantage of the propane/propylene price differential.

It is thus an object of the present invention to provide an improved process for the ammoxidation of paraffins to unsaturated nitriles.

It is a further object of the invention to provide new catalyst systems for such process.

Still another object is to provide an improved catalytic ammoxidation process for making unsaturated nitriles from lower paraffins without the use of halogen promoters.

Other objects, as well as aspects, features and advantages, of the present invention will become apparent from a study of the accompanying disclosure and the claims.

The foregoing and other objects of the present invention are achieved by the process of the present invention. There are two main features of the present invention. The first of these is the use of an excess of the alkane feed with relation to NH$_3$ and molecular oxygen. The second feature, which is used in combination with the high ratio of the C$_3$ to C$_5$ paraffin to NH$_3$ and O$_2$, is that a combination, i.e., a mixture, of catalysts is employed, the first catalyst composition being especially effective to promote formation of an unsaturated nitrile and an olefin from the paraffin, and the second catalyst composition being especially effective to promote the conversion of the olefin to the unsaturated nitrile. Such mixture is the subject of the composition claims herein.

In the present application "paraffin" designates an acyclic paraffin.

British Patent Specifications Nos. 1,336,135 and 1,336,136 disclose the use of high ratios of propane or isobutane to ammonia and oxygen, but only single ammoxidation catalysts are used, and the yields of acrylonitrile are extremely poor. U.S. Pat. No. 3,860,534 also discloses use of such high ratios, using a catalyst containing only V and Sb oxides. However, after the catalyst is calcined, it is washed for 24 hours with water and dried, a laborious procedure. A.N. Shatalova et al. in Neftekhiniya 8, No. 4, 609-612 (1968), describe the reaction of propane with oxygen and ammonia using a large excess of propane and a mixture of two catalysts, one of which is described as oxides of metals having dehydrogenating characteristics at 550 and 600° C. At 500° C. little or no acrylonitrile was produced. Rather large amounts of propionitrile and acrolein were made per mole of acrylonitrile produced. The per pass conversion of propane to acrylonitrile was generally 2–4 percent with selectivity to acrylonitrile being from 12 to 33 percent.

In the present process when applied to propane ammoxidation a small amount of propylene is produced in relation to the unreacted propane in the effluent. Such propane effluent containing propylene in the amount of up to 8 mole percent, but usually no more than 6 mole percent, of the amount of propane plus propylene can comprise the substrate feed to the present process. And in general the C$_3$ to C$_5$ alkane feed to the process can contain one or more C$_3$ to C$_5$ olefins. The C$_3$ to C$_5$ olefin content of the feed to the present ammoxidation process can contain from zero to 8 mole percent of such olefin(s), based on the moles of C$_3$ to C$_5$ paraffin plus olefins fed, and this feed can be from any source. Although larger amounts of C$_3$ to C$_5$ olefins may be present in the substrate paraffin feed, usual amounts are as stated, and the usual olefin is that corresponding to the particular paraffin fed to the reaction zone of the present process.

According to the present invention there is provided a process for the ammoxidation of a C$_3$ to C$_5$ paraffin to an $\alpha,\beta$-unsaturated mononitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:NH$_3$ in the range from 2 to 16 (usually 3–7), and a mole ratio of paraffin to O$_2$ in the range from 1 to 10 (usually 1.5–5), said first catalyst composition being 10–99 weight percent of a diluent/support and 90-1 weight percent of a catalyst having the components in the proportions indicated by the empirical formula:

where

A is one or more of W, Sn, Mo, B, P and Ge;

D is one or more of Fe, Co, Ni, Cr, Pb, Mn, Zn, Se, Te, Ga, In and As;

E is one or more of an alkali metal and Tl;

T is one or more of Ca, Sr and Ba; and where m is from 0.01 and up to 20; a is 0.2-10; b is 0-20; c is 0-20 (usually 0-1); t is 0-20; the ratio (a+b+c+t):(1+m) is 0.01-6; wherein x is determined by the oxidation state of the other elements, and wherein the antimony has an average valency higher than +3 and the vanadium has an average valency lower than +5, said second catalyst composition being 0–99 weight percent of a diluent/support and 100-1 weight percent of a catalyst having the components in the proportions indicated by the empirical formula:

where

Me is V, Mo, W or a combination of these;

G is one or more alkali metals;

Q is one or more of Cu, Mg, Zn, La, Ce, Cr, Mn, Co, Ni, Bi, Sn;

R is one or more of P, B and $d=10$–$60$, $e=0$–$10$, $f=0$–$6$, $g=0$–$5$, $h=0$–$10$, $i=0$–$5$, and x is a number deteremined by the valence requirements of the other elements present, and wherein the weight ratio in said mixture of said first catalyst composition to said second catalyst composition is in the range of 0.001 to 2.5.

In an especially useful catalyst of formula (1), m is greater than 1 (often 2–10, more often 3–7).

By "particulate mixture' as used herein is meant a mixture of solid particles or subdivided pieces of the first catalyst composition with separate and distinct solid particles of the second catalyst composition. The particles are often of a size used in fluidized bed reactors, say about 40 to 90 microns, but of course larger particles of catalyst can be employed for use in fixed or gravity flowing catalyst beds.

In the present process in all its embodiments the ratio of $O_2$ to $NH_3$ fed to the reaction zone is usually in the range from 1 to 10 (more often 1–5) and the ratio of inert gaseous diluent to paraffin is usually in the range zero to 5 (more often zero to 3).

The diluent or support for either catalyst composition is a refractory metal oxide or mixture, such as silica, silica-alumina, etc.

In the usual practice of the present invention the catalyst support/diluent for the catalyst of formula (1) is not an oxide of an element named in formula (1). Further, in the usual practice of the invention the catalyst support/diluent for the catalyst of formula (2) is not an oxide of an element named in formula (2).

In the catalyst compositions of the invention the catalyst empirical formulas (1) and (2) do not, of course, connote any particular chemical compound, nor indicate whether the elements are present as a mixture of individual oxides or as a complex oxide or oxides, or what separate crystalline phases or solid solutions may be present. Similarly, the designation of certain oxides, such as "silica' or "alumina' or $SiO_2$ or $Al_2O_3$, as supports or diluents is merely in accordance with convention in the inorganic oxide catalyst art, and such designations refer to compounds often regarded as supports in the catalyst art. Such designations, however, do not mean that the element involved is actually present as a simple oxide. Indeed, such elements may at times be present as a complex oxide with one, more than one, or all of the elements in formula (1) or formula (2), which complex oxides form during the precipitation or agglomeration, drying and calcining process for preparing the catalyst composition.

The process of the invention is especially useful in the ammoxidation of propane or isobutane.

According to the present invention the foregoing first catalyst composition is prepared under conditions such that in the final composition the average oxidation state of vanadium is less than 5.

One method for preparing the first catalyst composition is by a redox reaction between a compound of trivalent antimony such as $Sb_2O_3$ and a compound of pentavalent vanadium such as $V_2O_5$, during which the antimony is oxidized and the vanadium reduced.

The foregoing redox reaction was described by Birchall and Sleight (*Inorganic Chem.* 15, 868–70 [1976]) and by Berry et al. (*J. Chem. Soc. Dalton Trans.*, 1983, 9–12), who effected the reaction by heating a dry mixture of the above reactants at temperatures above 600° C. This product had a tetragonal rutile-type crystalline structure with a unique x-ray diffraction pattern.

However, it has been found that the redox reaction can successfully and more conveniently be carried out in an aqueous medium by heating at a temperature of at least 80° C. and up to 200° C., for instance, by heating an aqueous dispersion of a V5+compound, such as $NH_4VO_3$ or $V_2O_5$, with an Sb3+compound, such as by reacting $Sb_2O_3$ and $NH_4VO_3$ (or $V_2$ This step is followed by evaporation, drying and then calcining the product in a molecular oxygen-containing atmosphere, such as air, at from 350 to 700° or 750° C., usually 400° to 650° C. The length of the calcination period may range from 30 minutes to 12 hours, but satisfactory catalyst compositions are usually obtained by calcination at such temperatures for a period of from 1 to 5 hours.

At least part of any excess of trivalent antimony compound, such as $Sb_2O_3$, is usually oxidized to $Sb_2O_4$ during the calcination in a molecular oxygen-containing atmosphere, such as air.

The ingredients of the first catalyst composition other than vanadium and antimony (and of course part of the oxygen) suitably can be incorporated after completion of the foregoing redox reaction. Thus, the additives A, D, E and/or T, if any, can be added in the slurry after the redox reaction, or the solid particles containing the vanadium and antimony values after separation from the aqueous medium can be coated or impregnated in a known manner with such additives at any suitable stage prior to final calcination of the catalyst, by methods generally known in the art, using oxides, hydroxides, acids, salts (particularly organic salts such as acetates), and other compounds of such elements.

In formula (1) subscript a usually is at least 0.4 or 0.5. In formula (1) at least 0.2 atoms of W are usually present per atom of V, and the total of W plus Sn atoms (if any Sn is present) is usually at least 0.4 atoms. Preferred compositions of formula (1) contain at least 0.4 atoms of W per atom of V. Particularly when W is present, it is especially useful to have at least 0.4 atoms of P per atom of V in addition to the W. Especially useful are such compositions wherein said diluent/support comprises 20–100 weight percent alumina and 80 to zero weight percent silica.

Especially useful catalysts of formula (1) description are those in which a is at least 1, wherein A includes at least 1 atom of W.

Not only does the catalyst support in the first catalyst composition (formula (1)) improve mechanical stability of the catalyst, but also the catalytic activity is significantly improved, especially in the case of alumina and silica-alumina. Besides alumina and silica-alumina other supports that can be used are silica, titania, silica-titania, $Nb_2O_5$, silica-niobia, silica-zirconia, zirconia and magnesia, etc.

In the first catalyst composition, now preferred support materials for not only improving mechanical stability but also for improving the yield of the desired nitriles are selected from silica-alumina and alumina having 20–100, usually 50–100, preferably 60–100 weight percent alumina; silica-titania and titania having 20–100 weight percent titania; silica-zirconia and zirconia having 80–100 weight percent zirconia; and silica-niobia and niobia having 30–100 weight percent niobia ($Nb_2O_5$).

In the preparation of the second catalyst composition of formula (2) the metal oxides can be blended together or can be formed separately and then blended or formed separately or together in situ. Promoter oxides, if any, are preferably incorporated into the iron-antimony based catalyst by blending into the gel before calcining or by blending into the oven-dried base catalyst before calcining. A preferred manner of incorporating promoter elements is by choosing a water-soluble salt of the promoter element, forming an aqueous solution of the salt, and mixing the solution with a solution or a suspension of the base elements or salts thereof. Optionally, the promoter elements can be incorporated by the use of soluble complex salts or compounds with the desired base elements which upon calcination will yield the desired ratio of the elements in the finished catalyst.

To introduce the iron component into the catalyst one may use any compound of iron which, upon calcination, will result in the oxides. As with the other elements, water soluble salts are preferred for the ease with which they may be uniformly dispersed within the catalyst. Most preferred is ferric nitrate. Cobalt and nickel are similarly introduced.

Antimony is suitably introduced as $Sb_2O_3$, or an $Sb_2O_5$ sol can be used. It is also possible to add finely divided antimony metal to concentrated nitric acid and then to boil the slurry to decompose the excess nitric acid, leaving an antimony oxide slurry.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result, upon heating to a temperature within the range disclosed hereinafter, in the oxides of the instant catalyst.

These second catalyst compositions are conveniently prepared by slurry techniques wherein an aqueous slurry containing all of the elements in the objective catalyst is produced, the water removed from the aqueous slurry to form a precatalyst precipitate or powder and the precatalyst then heated in the presence of an oxygen-containing gas such as air at elevated temperature to calcine the precatalyst thereby forming the catalyst. Liquids other than water, such as $C_1$ to $C_8$ alcohols can also be used to form the precatalyst slurry.

In the second catalyst composition the support can be any of the usual supports such as silica, alumina, silica-alumina, titania, zirconia, and $Nb_2O_5$.

In the ammoxidation of the present invention, the reaction is carried out in the gas phase by contacting a mixture of the paraffin, ammonia and molecular oxygen, and inert diluent, if any, conveniently in a fixed bed of the catalyst mixture, or a gravity flowing bed, a fluidized bed or a fast transport reactor mode.

Examples of inert diluents useful in the reaction are $N_2$, He, $CO_2$, $H_2O$ and Ar.

The reaction temperature range can vary from 350° to 700° C., but is usually 430° to 520° C. The latter temperature range is especially useful in the case of propane ammoxidation to acrylonitrile.

The average contact time can often be from 0.01 to 10 seconds, but is usually from 0.02 to 10 seconds, more usually from 0.1 to 5 seconds.

The pressure of the reaction usually ranges from 2 to 45 psia. Most often, pressure is somewhat above atmospheric.

The following examples of the invention are exemplary and should not be taken as in any way limiting.

EXAMPLE 1

A catalyst having the empirical formula 50 wt % $VSb_5WO_x$+50 wt % $Al_2O_3$ support was made as follows:

In a stirred flask equipped for heating under reflux, 5.4g $NH_4VO_3$ was dissolved in 150ml hot water. To the hot solution 33.6g $Sb_2O_3$ was added, and the slurry was boiled under reflux for 16–18 hours overnight. There was ammonia evolution, and the vanadium antimony oxide mixture turned gray-green.

In a separate operation, 59.0g Catapal SB (hydrated alumina) was mixed with 200ml $H_2O$ (cold) +23.0g acetic acid (10 percent solution) and stirred until the suspension gelled. It took about 3 hours, and the gel was soft, homogenous, with the consistency of thick cream.

Meanwhile, the vanadium antimony slurry was transferred to a beaker. A solution of 12.5g ammonium metatungstate in about 25ml $H_2O$ was then added, followed by the addition, with stirring (magnet) of the alumina gel. After partial evaporation, the mixture became too thick for stirring. It was then transferred to an evaporating dish, and the evaporation, following by drying overnight, was continued in an oven at 110°-120° C. The dried material was precalcined at 350° C. for 5 hours, screened to 20/35 mesh, then calcined 3 hours at 610° C.

EXAMPLE 2

A catalyst having the empirical formula 50 wt % $VSb_{3.5}P_{0.5}WO_x$+50 wt % $Al_2O_3$ support was made as follows:

In a stirred flask equipped for heating under reflux, 3.81g $NH_4VO_3$ were dissolved in 90ml hot water. To the hot solution 16.6g $Sb_2O_3$ were added, and the slurry was boiled under reflux for 16-18 hours overnight. There was ammonia evolution, and the vanadium antimony mixture turned gray-green.

In a separate operation, 35.3g Catapal SB (hydrated alumina) were mixed with 127.2ml $H_2O$ (cold) +14.1g acetic acid (10 percent solution) and stirred until the suspension gelled. It took about 3 hours, and the gel was soft, homogeneous, with the consistency of thick cream.

Meanwhile, the vanadium antimony slurry was transferred to a beaker. A solution of 8.80g ammonium metatungstate in about 20ml $H_2O$ and a solution of 1.77g $(NH_4)_2HPO_4$ in $H_2O$ were then added, followed by the addition, with stirring (magnet) of the alumina gel. After partial evaporation, the mixture became too thick for stirring. It was then transferred to an evaporating dish, and the evaporation, following by drying overnight, was continued in an oven at 110°-120° C. The dried material was precalcined at 350° C. for 5 hours, screened to 20/35 mesh, then calcined 3 hours at 610° C.

EXAMPLE 3

88.36g of $Fe(NO_3)_3 \cdot 9H_2O$ were dissolved in 170cc of water with stirring; this solution was added to 687.86g of a 12 weight percent $Sb_2O_5$ sol with stirring. A cloudy, light brown gel formed which broke up with rapid stirring. The dispersion was concentrated by heating and then dried in an evaporating dish overnight in a drying oven at 130° C. Thereafter, it was heat treated at 290° C. for 3 hours and at 425° C. for 3 hours, then calcined by heating at 610° C. for 3 hours. The catalyst was ground to 20-35 mesh size. Its composition was $Fe_3Sb_7O_x$.

EXAMPLE 4

A catalyst having the empirical composition 60 wt% $Fe_{10}Sb_{20}Cu_{3.2}Te_{1.36}Mo_{0.57}W_{0.083}V_{0.15}O_x + 40$ wt% $SiO_2$ Solution 1: 38.4 lbs of dionized water (D.I. $H_2O$) was added to a container and heated to 80° C. Then 88.9g of ammonium paratungstate was dissolved therein and the temperature lowered to about 50°–60° C. Then 72.8g of ammonium metavanadate was dissolved in this solution and the temperature was then lowered to 35°–40° C. Later, 406g of ammonium paramolybdate was dissolved in the solution and the temperature was adjusted to 30°–35° C.

Solution 2: To another container were added 120 lbs of a metal nitrate aqueous solution containing in weight percent: 4.27% Fe, 1.49% Cu, 1.30% Te and 23.7% $-NO_3$. To this solution were added 808 pounds of 70.2 weight percent $HNO_3$.

To a 50 gallon vessel, having a reflux condenser and a stirrer were added 71.8 pounds of D.I. $H_2O$ and 71.8 pounds of a 40 weight percent silica sol ($NH_3$ stabilized). While stirring all of Solution 2 was added and stirred for 5 minutes. Then 26.3 pounds of $Sb_2O_3$ were added, and then all of Solution 1 was added and stirring was continued for 5 minutes.

Thereafter, over a period of 50–60 minutes, 45.8 pounds of 14.7 weight % aqueous $NH_3$ solution were added while keeping the temperature at 32°–38° C. The pH was measured at about 40° C. and was found to be 2.35.

The slurry was then heated to reflux (about 100° C.) over a period of 1 hour, and thereafter was refluxed for 4 hours. Thereafter, a portion of the slurry was transferred to an evaporating dish, and the evaporation and drying was effected in an oven overnight at 110°–120° C. The dried material was heated at 290° C. for 3 hours and 425° C. for 3 hours, then ground to 20–35 mesh and calcined by heating at 825° C. for 3 hours.

In the ammoxidation runs of the following examples, the catalyst, or the mixture of catalysts, is in a tubular ⅜ inch I.D. stainless steel fixed bed reactor. When a mixture of particulate catalysts is used, as in the invention examples, the desired weight of each of the two catalyst compositions is put in a vial and shaken until uniformly dispersed before placing the desired amount of the catalyst mixture in the reaction tube. The reaction is equipped with a preheat leg and is immersed in a temperature controlled molten salt bath. The gaseous feed components are metered through mass flow controllers into the bottom of the reactor through the preheat leg. Water is introduced through a septum at the top of the preheat leg, using a syringe pump. The feed is fed to the catalyst for 1 hour before collection of product; the runs of each example last 30 minutes during which the product is collected for analysis.

EXAMPLE 5

In this example the catalyst was a mixture of the catalyst of Example 1 and the catalyst of Example 4 in the weight ratio of the former to the latter of 0.20. The reaction temperature was 470° C. and the molar feed ratios were 5 propane/1 $NH_3$/2 $O_2$/1 $H_2O$. The contact time was 1.8 seconds. Analysis of the reactor effluent showed that propane conversion was 12.0 percent; yield and selectivity of propane to acrylonitrile were 2.8 and 23.3 percent, respectively; selectivity to propylene was 38.3 percent.

COMPARATIVE EXAMPLE A

In this example the reaction temperature was 470° C. and the molar feed ratios were 5 propane/1 $NH_3$/2 $O_2$/1 $H_2O$. The catalyst was the catalyst of Example 1 alone. The contact time was 0.2 seconds. Analysis of the reactor effluent showed that propane conversion was 16.9 percent; yield and selectivity of propane to acrylonitrile were 3.3 and 19.5 percent respectively; selectivity to propylene was 50.6 percent.

EXAMPLE 6

In this example the catalyst was a mixture of the catalyst of Example 2 and the catalyst of Example 3 in the weight ratio of the former to the latter of 0.15. The reaction temperature was 470° C. and the molar feed ratios were 5 propane/1 $NH_3$/2 $O_2$/1 $H_2O$. The contact time was 2.2 seconds. Analysis of the reactor effluent showed that propane conversion was 14.5 percent; yield and selectivity of propane to acrylonitrile were 5.3 and 36.5 percent, respectively; selectivity to propylene was 27.4 percent.

COMPARATIVE EXAMPLE B

In this example the reaction temperature was 470° C. and the molar feed ratios were 5 propane/1 $NH_3$/2 $O_2$/1 $H_2O$. The catalyst was the catalyst of Example 2 alone. The contact time was 0.3 seconds. Analysis of the reactor effluent showed that propane conversion was 18.3 percent; yield and selectivity of propane to acrylonitrile were 3.7 and 20.4 percent, respectively; selectivity to propylene was 52.8 percent.

COMPARATIVE EXAMPLE C

In this example the reaction temperature was 470° C. and the molar feed ratios were 5 propane/1 $NH_3$/2 $O_2$/1 $H_2O$. The catalyst was the catalyst of Example 3 alone. The contact time was 0.8 seconds. Analysis of the reactor effluent showed that propane conversion was 2.9 percent; yield and selectivity of propane to acrylonitrile were 1.2 and 42.1 percent; selectivity to propylene was 15.9 percent.

EXAMPLE 7

In this example the catalyst was a mixture of the catalyst of Example 2 and the catalyst of Example 4 in the weight ratio of the former to the latter of 0.15. The reaction temperature was 470° C. and the molar feed ratios were 5 propane/1 $NH_3$/2 $O_2$/1 $H_2O$. The contact time was 1.5 seconds. Analysis of the reactor effluent showed that propane conversion was 10.6 percent; yield and selectivity of propane to acrylonitrile were 3.5 and 32.4 percent, respectively; selectivity to propylene was 34.0 percent.

As will be evident to those skilled in the art various modifications of this invention can be made or followed in the light of the foregoing disclosure and discussion without departing from the spirit and scope of the disclosure or from the scope of the claims.

We claim:

1. A process for the ammoxidation of a $C_3$ to $C_5$ paraffin to an $\alpha,\beta$-unsaturated mononitrile which comprises contacting in a reaction zone said paraffin in the vapor phase in admixture with ammonia, molecular oxygen, and optionally an inert gaseous diluent, with an intimate particulate mixture of a first catalyst composition and a second catalyst composition, said feed to the reaction zone containing a mole ratio of paraffin:$NH_3$ in the range from 2 to 16 and a mole ratio of paraffin to $O_2$ in the range from 1 to 10, said first catalyst composition being 10–99 weight percent of a diluent/support and 90–1 weight percent of a catalyst having the components in the proportions indicated by the empirical formula:

$$VSb_mA_aD_bE_cT_tO_x, \qquad \text{formula (1)}$$

where

A is one or more of W, Sn, Mo, B, P and Ge;

D is one or more of Fe, Co, Ni, Cr, Pb, Mn, Zn, Se, Te, Ga, In and As;

E is one or more of an alkali metal and Tl;

T is one or more of Ca, Sr and Ba; and where m is from 0.01 and up to 20; a is 0.2–10; b is 0–20; c is 0–, t is 0–20; the ratio (a+b+c+t):(1+m) is 0.01–6; wherein x is determined by the oxidation state of other elements, and wherein the antimony has an average valency higher than +3 and the vanadium has an average valency lower than +5, said second catalyst composition being 0–99 weight percent of a diluent/support and 100–1 weight percent of a catalyst having the components in the proportions indicated by the empirical formula:

$$Fe_{10}Sb_dTe_eMe_fG_gQ_hR_iO_x \qquad \text{formula (2)}$$

where

Me is V, Mo, W or a combination of these;

G is one or more alkali metals;

Q is one or more of Cu, Mg, Zn, La, Ce, Cr, Mn, Co, Ni, Bi, Sn;

R is one or more of P, B and, d=10–60, e=0–10, f=0–6, g=0–5, h=0–10, i=0–5, and x is a number determined by the valence requirements of the other elements present, and wherein the weight ratio in said mixture of said first catalyst composition to said second catalyst composition is in the range of 0.001 to 2.5.

2. A process of claim 1 wherein said mole ratio of paraffin:$NH_3$ is in the range from 3 to 7.

3. A process of claim 1 wherein said mole ratio of paraffin:$O_2$ is in the range from 1.5 to 5.

4. A process of claim 2 wherein said mole ratio of paraffin:$O_2$ is in the range from 1.5 to 5.

5. A process according to claim 1 wherein the mole ratio of $O_2$ to $NH_3$ in the feed to the reaction zone is in the range from 1 to 10.

6. A process according to claim 1 wherein the mole ratio of inert gaseous diluent to paraffin in the feed to the reaction zone is in the range from zero to 5.

7. A process of claim 1 wherein A includes at least 0.2 atoms of W per atom of V and the total A atoms include at least 0.4 (w atoms +Sn atoms) per atom of V.

8. A process of claim 1 wherein A includes a least 0.4 atoms of P per atom of V.

9. A process of claim 1 wherein said support for the catalyst of formula (1) is selected from silica, alumina, titania, silica-niobia, silica-zirconia, silica-titania, silica-alumina, $Nb_2O_5$ and magnesia.

10. A process of claim 1 wherein said support for the catalyst of formula (1) is selected from silica-alumina and alumina having 20–100 weight percent alumina; silica-titania and titania having 20–100 weight percent titania; silica-zirconia and zirconia having 80–100 weight percent zirconia; and silica-niobia and niobia having 30–100 weight percent niobia ($Nb_2O_5$).

11. A process of claim 1 wherein m is 2–10.

12. A process of claim 1 wherein m is 3–7.

13. A process of claim 1, wherein said diluent/support in said first catalyst composition comprises 20–100 weight percent alumina and 80 to zero weight percent silica.

14. A process of claim 13 wherein said diluent/support in said first catalyst composition comprises 50–100 weight percent alumina and 50 to zero weight percent silica.

15. A process of claim 1 wherein said paraffin is propane or isobutane.

16. A process of claim 1 wherein said paraffin is propane.

17. A process of claim 11 wherein said paraffin is propane or isobutane.

18. A process of claim 13 wherein said paraffin is propane or isobutane.

* * * * *

UNITED STATES PATENT AND TRADEMARK OFFICE
CERTIFICATE OF CORRECTION

PATENT NO. : 4,801,727
DATED     : January 31, 1989
INVENTOR(S) : Glaeser et al

It is certified that error appears in the above-identified patent and that said Letters Patent is hereby corrected as shown below:

Column 9, Line 19, Claim 1, "c is 0-," should read --c is 0-1;--

Column 9, Line 21, Claim 1, after "elements", should read --; A includes at least 0.2 atoms of W per atom of V--

Column 10, Line 13, Claim 7, "w" should read --W--.

Signed and Sealed this

Twenty-seventh Day of June, 1989

Attest:

DONALD J. QUIGG

Attesting Officer

Commissioner of Patents and Trademarks